United States Patent [19]

Wolff, III et al.

[11] 4,310,550
[45] Jan. 12, 1982

[54] LIPID AMINES FORMULATED WITH FAT OR LIPID EMULSIONS AS VACCINE ADJUVANTS

[75] Inventors: John S. Wolff, III, River Vale; George R. Hemsworth, Sparta, both of N.J.; Keith E. Jensen, Waterford, Conn.

[73] Assignee: Pfizer Inc., New York, N.Y.

[21] Appl. No.: 88,638

[22] Filed: Oct. 26, 1979

[51] Int. Cl.³ .................. A61K 31/13; A61K 31/685; A61K 39/00; A61K 47/00
[52] U.S. Cl. ..................................... 424/365; 424/88; 424/199; 424/325; 424/330; 424/358
[58] Field of Search ............... 424/199, 358, 325, 330, 424/365

[56] References Cited

U.S. PATENT DOCUMENTS

| | | | |
|---|---|---|---|
| 3,169,094 | 2/1965 | Wrettind | 424/199 |
| 3,872,171 | 3/1975 | Cronin et al. | 424/298 |
| 4,034,040 | 7/1977 | Cronin et al. | 424/330 |
| 4,173,641 | 11/1979 | Kraska | 424/267 |

OTHER PUBLICATIONS

Gall, Immunology 11, pp. 369–386, (1966).
Strannegard et al.; Int. Arch Allergy appln. Immun. 51, pp. 198–205 (1976).
"Immunological Adjuvants", World Health Organization Technical Report Series No. 595 (1976).
Fortner et al., Am. J. Hosp. Pharm. 32, pp. 582–584 (1975).
Chang and Pearson, Arth. Rheum. 21, pp. 169–170 (1978).

Primary Examiner—Stanley J. Friedman
Attorney, Agent, or Firm—Connolly and Hutz

[57] ABSTRACT

N,N-higher alkyl-N',N'-bis(2-hydroxyethyl)propanediamines and N,N-higher alkyl-xylylenediamines formulated with fat or lipid emulsions are useful as vaccine adjuvants of low toxicity. These compositions are useful in conjunction with known immunological substances in order to induce or enhance the immunogenic response. Preferred compositions employ N,N-higher alkyl-N',N'-bis(2-hydroxyethyl)propanediamines, particularly N,N-dioctadecyl-N',N'-bis(2-hydroxyethyl)propanediamine in Intralipid.

6 Claims, No Drawings

LIPID AMINES FORMULATED WITH FAT OR LIPID EMULSIONS AS VACCINE ADJUVANTS

BACKGROUND OF THE INVENTION

The need for an adjuvant in the administration of immunological substances has long been recognized and considerable work has been done to discover substances which when added to an antigen or other immunological substance would potentiate its antigenic activity and thereby its antibody stimulating capacity. To date, many such adjuvants have been discovered such as the use of alum precipitation of antigens, combining certain specific antigens some of which would potentiate the activity of the others in the mixture, the use of calcium phosphate particularly to potentiate influenza antibody production and the similar use of Staphylococcus toxin which appear to improve the antibody response to certain antigens. Several other adjuvant substances also have been considered such as tapioca, calcium or magnesium salts, tannin and the like which when added to certain specific antigens would increase the antibody titer over that obtainable when the antigen alone was administered.

Immunological adjuvants are used to increase the amount of antibody produced and to reduce the quantity of antigen and the frequency of injection. Aluminum adjuvants are widely used, and although considered safe in man, sterile abscesses and persistent nodules may follow their use. Complete Freund's adjuvant, an oil-in-water emulsion containing tubercle bacilli, is more potent than the aluminum adjuvants. However, the deleterious side effects, including severe granuloma formation, allergic responses, and oil retention in the tissues, preclude its use in man.

The present invention represents the development of a potent, well-tolerated adjuvant for incorporation in a range of vaccines and antigen compositions for use in man and animals. The antigen itself may be in the form of purified or partially purified antigen derived from bacteria, viruses, or rickettsia, or the antigen may be an allergen such as pollens, dusts, danders, or extracts of the same or the antigen may be in the form of a poison or a venom derived from poisonous insects or reptiles. In all cases the antigen will be in the form which when introduced into a suitable host will either induce active immunity by the production therein of antibodies against the specific antigen or, in the case of an allergen, will aid in alleviating the symptoms of the allergy due to the specific allergen. The antigens can be used either singly or in combination. Antigens of particular importance are derived from bacteria such as *H. pertussis, Leptospira pomona* and *icterohaemorrhagiae, S. typhosa, S. paratyphi* A and B, *C. diphtheriae, C. tetani, C. botulinum, C. perfringens, C. feseri* and other gas gangrene bacteria, *B. anthracis, P. pestis, P. multocida, V. cholerae* and the like; from viruses as poliovirus (multiple types), adeno virus (multiple types), parainfluenza virus (multiple types), measles, mumps, respiratory syncytial virus, influenza (multiple types), shipping fever virus (SF4), Western and Eastern equine encephalomyelitis, Japanese B. encephalomyelitis, Russian Spring Summer encephalomyelitis, hog cholera virus, fowl pox, Newcastle disease virus, rabies, feline and canine distemper and the like viruses, from rickettsiae as epidemic and endemic typhus or other members of the spotted fever group, from various spider and snake venoms or any of the known allergens such as ragweed, house dust, pollen extracts, grass pollens and the like.

A number of substances, some of which are also inducers of interferon, have been reported to have adjuvant properties. These are listed in "Immunological Adjuvants," World Health Organization Technical Report Series No. 595. In addition to this list is the reported adjuvant activity of aliphatic nitrogeneous bases by D. Gall, Immunology, 11, 369 (1966) and lysolecithin analogues by O. Shannegard and G. Roupe, Int. Arch. Allergy Appln. Immun., 51, 198 (1976).

SUMMARY OF THE INVENTION

The present invention is concerned with compounds of the formulae I and II

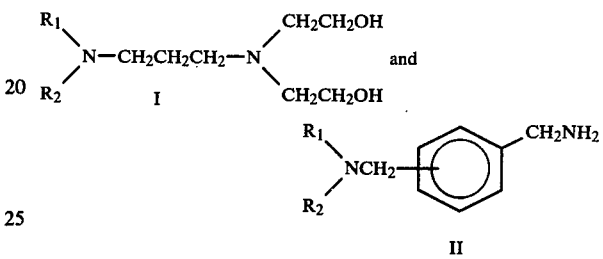

wherein $R_1$ and $R_2$ are each alkyl of 12 to 20 carbon atoms; and their pharmaceutically acceptable acid addition salts which are useful as vaccine adjuvants and may be used for the purposes and administered by the same methods as presently known adjuvants, see for example, "Immunological Adjuvants," World Health Organization Technical Report Series, No. 595. For example, the compounds of the present invention are useful as adjuvants when used in conjunction with vaccines such as, but not limited to, those for influenza, foot and mouth disease and diphtheria. The compound may be incorporated in the vaccine, preferably in a pharmaceutically acceptable carrier such as a fat or lipid emulsion, glycerol, 2-pyrrolidone, mineral oil, etc. The optimal formulation vehicle is a fat or lipid emulsion, in particular a 10% intravenous fat emulsion sold under the trademark of Intralipid 10% for use in patients requiring parenteral nutrition for extended periods. Intralipid 10%, available from Cutter Laboratories, Inc., Berkeley, California, is made up of 10% soybean oil, 1.2% egg yolk phospholipids, 2.25% glycerin, water for injection and sodium hydroxide sufficient to adjust the pH between 5.5 and 9.0. While this particular emulsion is not required for adjuvant activity, since augmented responses to various antigens are seen with the present compounds in mineral oil vehicles, in Tween-80 dispersions in saline, 2-pyrrolidone, etc., the local toxicity of these compounds is minimized in this vehicle. The vaccine-adjuvant is then administered to the subject in the manner conventional for the particular vaccine, generally as a single dose of an antigen in saline combined with the compound in lipid emulsion, administered subcutaneously or intramuscularly. Alternatively, the adjuvant may be administered independently of the vaccine.

DETAILED DESCRIPTION OF THE INVENTION

The present invention is concerned with the adjuvant properties of N,N-higher alkyl-N',N'-bis(2-hydroxyethyl)-propanediamines and N,N-higher alkylxylylenediamines. The preparation and properties of these compounds are described in U.S. Pat. Nos. 3,872,171 and 4,034,040.

Comparison studies were performed in guinea pigs (Camm Laboratories, Wayne, N.J. and Springfield Laboratories, Springfield, N.Y.) on the primary and secondary antibody responses obtained after injection with appropriate lipid amines incorporated in different vehicles and appropriate controls each combined with cellular antigens such as sheep red blood cells and EL4 cells and a viral antigen such as influenza virus (Fluogen, Parke-Davis, Detroit, Michigan).

MATERIALS AND METHODS

Preparation of Adjuvant Compositions

The lipid amines were each dissolved in 0.3 ml of absolute ethanol, 0.1 ml of Tween 80 (polyoxyethylene monooleate—ICI, Wilmington, Delaware) and hand mixed with 4.6 ml of Intralipid (Cutter Laboratories, Fairfield, N.J.)—an aqueous fat emulsion comprising 10% soybean oil, 1.2% egg yolk phospholipids, 2.25% glycerol and sufficient water to bring the volume to 100%.

Preparation of Antigen Compositions

Sheep red blood cells bled directly into Alsever's solution were washed with 0.85% saline and adjusted to a cell concentration of $1.8 \times 10$ per ml of saline. Two ml of sheep red blood cell suspension was added to 5.0 ml of each adjuvant.

Two ml of Fluogen was mixed with each 5 ml of each adjuvant such that each 0.5 ml injection volume contained 250 CCA of antigen.

EL4 cells were suspended in saline, $5 \times 10^7$ cells per 0.4 ml, Complete Freund's Adjuvant, and in a solution of lipid amine in mineral oil (50 mg/ml).

Immunization

Experimental groups of animals were treated intramuscularly as follows:
(1) 0.5 ml of each antigen in each adjuvant diluent.
(2) 0.5 ml of each antigen without adjuvant diluent.
(3) 0.5 ml of each adjuvant diluent.

Antigen Challenge

Approximately 30 days after sensitization, animals were challenged by intramuscular administration of homologous antigen in saline into the opposite leg.

Serum Preparation

Animals were bled by intracardiac puncture at several times after primary sensitization and the separated serum stored at $-20°$ until titration.

Immune Response

Sheep Red Blood Cells
1. Hemagglutination Titer

Serum (0.25 ml) was serially diluted in phosphate buffered saline in microtiter plates. Then 0.5 ml of an 0.5% sheep red blood cell suspension in 100-fold diluted fetal calf serum previously absorbed with packed sheep red blood cells was added to each well. The highest titer giving visible agglutination was scored as the titer of the serum.

2. Delayed Hypersensitivity 0.1 ml of $1 \times 10^8$ suspension of sheep red blood cells was injected intradermally in the shaved and depilatated back of the guinea pig. After a period of 24 hours, the area of erythema was scored by measuring two perpendicular diameters, one of which was on the long axis if the spot was an oval. The intensity of erythema and induration was also scored, and tended to parallel roughly the area of reaction.

EL4 Cells

The humoral immune response to EL4 cells in rats (measured by complement dependent antibody lysis of $^{51}$Cr labeled EL4 cells) is described by Y. H. Chang in J. Phar. Exp. Ther. (in press) 1977.

Influenza Virus

Hemagglutination Inhibition Test

Test sera, treated with 0.111 M KIO4 to remove non-specific serum factors that inhibit agglutination, were dispensed in serial two-fold dilutions in 0.025 ml volumes into microtiter wells containing 0.025 ml of 0.01 M phosphate-buffered physiological saline, pH 7.2. The test virus suspension, containing 4 hemagglutination units per 0.025 ml of buffered saline, was added to each well. Buffered saline and antigen controls (buffered saline and virus antigen) were employed. After incubating the plates at room temperature for about 30 minutes, 0.05 ml of 0.5% saline washed chicken erythrocytes (Flow Laboratories, Rockville, Md.) was added to each well. Incubation was allowed to continue until the cell control (phosphate-buffered physiological saline only) showed normal settling. Periodate-treated sera from normal guinea pigs were included to assess the level of non-specific agglutination inhibition remaining in the KIO4 treated test sera. The hemagglutination titer was defined as the highest dilution of serum which completely inhibited hemagglutination, corrected for non-specific inhibition.

EXAMPLE 1

Antibody responses of guinea pigs vaccinated with sheep red blood cells in different vehicles were studied. Animals were bled fifteen days after vaccination, bled and challenged on the 30th day, and bled again on days 45 and 60. The results are shown in Table 1.

TABLE 1

Effect of N,N-dioctadecyl-N',N'-bis(2-hydroxyethyl)-propanediamine (Compound 20,961) on antibody titer to sheep red blood cells.

| | Serum Hemagglutination Titer | | |
|---|---|---|---|
| | 30[a] | 45 | 65 |
| Saline | 12 | 356 | 36 |
| Vehicle[b] | 10 | 526 | 39 |
| Vehicle and CP-20,961 (3 mg) | 1402 | 2739 | 1267 |

[a]Days after vaccination; eight animals per group.
[b]Intralipid-Tween-Ethanol.

Sheep red blood cells in saline or Intralipid induced no primary antibody response and only a transient secondary response but strong primary as well as secondary antibody responses to sheep red blood cells were observed in animals inoculated with sheep red blood cells containing Compound 20,961.

EXAMPLE 2

A study was conducted to determine an optimum dose of Compound 20,961 dissolved in ethanol mixed in the Tween 80-Interlipid adjuvant vehicle. Sheep red blood cells was used as the antigen and eight guinea pigs were immunized per group. Sheep red blood cells mixed with saline served as a comparison control. The results are shown in Table 2.

TABLE 2

The effect of the quantity of Compound 20,961 in the adjuvant on the response to sheep red blood cells.

| Quantity of CP-20,961 (mg) | Hemagglutination titer | Delayed Skin Test (Area in mm) |
|---|---|---|
| Vehicle* + 0 | 192 ± 81 | 174 ± 23 |
| Vehicle + 0.3 | 448 ± 64 | 172 ± 34 |
| Vehicle + 1.0 | 1741 ± 639 | 285 ± 35 |
| Vehicle + 3.0 | 2560 ± 887 | 374 ± 40 |
| Vehicle + 10.0 | 1024 ± 280 | 393 ± 62 |
| Saline | 51 ± 8 | 149 ± 11 |

*Intralipid

The data show that hemagglutination antibody titers rose progressively with doses of Compound 20,961 to a maximal titer at 3 mg/site. A further increase in the amount of Compound 20,961 to 10 mg/site resulted in a lower peak titer.

EXAMPLE 3

Adjuvant Compound 20,961 was examined for its ability to elicit a secondary response upon challenge with sheep red blood cell antigen in the absence of adjuvant. This may be considered a measure of the induction of immune memory. The guinea pigs were all given a booster injection on day 30 with sheep red blood cells alone, bled and their sera titered on days 45 and 65. The results are shown in Table 3.

TABLE 3

The primary and secondary response with sheep red blood cells in selected adjuvants.

| | Hemagglutination titer | | | |
|---|---|---|---|---|
| | Day 30 | Boost Day 30 | Day 45 | Day 65 |
| Saline | 12 + 2 | — | 356 ± 97 | 36 + 6 |
| Vehicle* | 10 ± 1 | — | 526 ± 217 | 39 ± 7 |
| Vehicle and CP-20,961 | 1402 ± 848 | — | 2739 ± 970 | 1267 ± 790 |

*Intralipid

Sheep red blood cells with Intralipid/Compound 20,961 (3 mg/site) elicited a potent primary response with red blood cells. Vehicle Intralipid containing sheep red blood cells did not elicit a primary response significantly different from sheep red blood cells in saline. Only sheep red blood cells in Intralipid/Compound 20,961 adjuvant gave strikingly enhanced titers on secondary response.

EXAMPLE 4

The methods of Example 1 and 2 may be repeated with comparable results employing a series of N,N-higher alkyl-N',N'-bis(2-hydroxyethyl)-propanediamines and N,N-higher alkyl-xylylenediamines wherein the higher alkyl groups contain 10 to 20 carbons in place of Compound 20,961.

EXAMPLE 5

A study was conducted to compare the primary antibody response to influenza virus incorporated with different vehicles. The results are shown in Table 4.

TABLE 4

Effect of CP-20,961 on influenza virus serum HI titer after vaccination.

| | Geometric mean serum HI titer | |
|---|---|---|
| Inoculum[a] | 15[b] | 30 |
| Saline | 2 | 17 |
| Vehicle[c] | 6 | 62 |
| Vehicle and CP-20,961 (10 mg) | 6 | 80 |

[a]Antigen was 250 CCA monovalent influenza virus. Injection route was intramuscular on day "0"
[b]Days after vaccination.
[c]Intralipid.

EXAMPLE 6

The immunized animals of Example 5 were given a second injection of influenza virus vaccine. The secondary immune responses are shown in Table 5.

TABLE 5

Serum titers at 2 and 5 weeks after secondary injection of influenza vaccine.

| | Geometric mean serum HI titer | |
|---|---|---|
| Group[a] | 2[b] | 5[b] |
| Saline | 28 (8)[c] | 5 (7) |
| Vehicle[d] | 80 (7) | 18 (6) |
| Vehicle and CP-20,961 | 349 (8) | 20 (8) |

[a]Animals received IM injection with 250 CCA influenza. vaccine in saline 30 days after sensitization.
[b]Weeks after challenge.
[c]Animals per group.
[d]Intralipid-Tween-Ethanol.

Antibody titers two weeks after a second injection of influenza virus vaccine were elevated about 10 fold (Intralipid+Compound 20,961) over titers obtained in the vaccine control group. Five weeks post-challenge, the titers of Intralipid+Compound 20,961 vaccinated animals were not different from controls.

EXAMPLE 7

Rats were injected intraperitoneally with a suspension of $5 \times 10^7$ EL$_4$ cells in 0.4 ml of saline and EL$_4$ cells in a solution of Compound 20,961 in mineral oil (50 mg/ml). The humoral response (reciprocal titers) is shown in Table 6.

TABLE 6

| Humoral immune response (reciprocal titers). | |
|---|---|
| EL$_4$ cells + saline | 4,933 |
| EL$_4$ cells + Compound 20,961 + mineral oil | 7,800 |

EXAMPLE 8

The methods of Examples 5, 6 and 7 may be repeated with comparable results employing a series of N,N-higher alkyl-N',N'-bis(2-hydroxyethyl)-propanediamines and N,N-higher alkyl-xylylenediamines wherein the higher alkyl groups contain 10 to 20 carbon atoms in place of Compound 20,961.

EXAMPLE 9

Egg lecithin (phospholipid, average molecular weight 880, 220 mg, 0.25 mmoles) dissolved in 2.2 ml of chloroform:methanol (9:1) was evaporated to dryness, for the most part under a stream of nitrogen and finally in vacuo. Absolute ethanol (22 ml) was added to the residue, which, together with Compound 20,961 (220 mg, 0.495 mmoles), was dissolved by warming to 37°–40° C. The solution was clarified by filtration through a glass fiber filter and 21 ml of filtrate added to 305 ml of an aqueous solution 0.15 M in sodium chloride and 0.005 M in sodium phosphate (pH 7.4). The diluted solution was again clarified by filtration and was then concentrated to 5 ml in an Amicon ultrafiltration cell with an XM100A filter membrane at 10 p.s.i. The concentrate was reconstituted to 30 ml with filtrate. Aggregates greater than or equal to five microns in size were present. The formulation was easily filtered through a 3 micron Nucleopore which decreased the aggregate size. This process provides a liposome type, lipid emulsion formulation of Compound 20,961 which is also suitable for parenteral co-administration with an antigen.

We claim:

1. A pharmaceutical composition, suitable for parenteral injection in man or animals, which comprises an effective amount of a compound of the formula

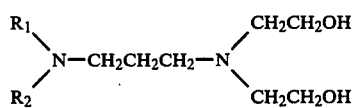

or

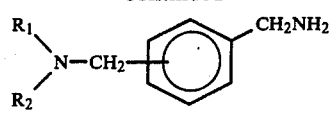

or a pharmaceutically acceptable acid addition salt thereof;

wherein $R_1$ and $R_2$ are each alkyl of 12 to 20 carbon atoms;

and a lipid or fat emulsion comprising about 10% vegetable oil and about 1.2% phospholipids.

2. A pharmaceutical composition of claim 1 wherein the compound is

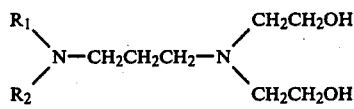

3. A pharmaceutical composition of claim 2 wherein the compound is N,N-dioctadecyl-N,N'-bis(2-hydroxyethyl)propanediamine.

4. A pharmaceutical composition of claim 1 wherein the lipid or fat emulsion is composed of 10% soybean oil and 1.2% egg yolk phospholipids.

5. A pharmaceutical composition of claim 2 wherein the lipid or fat emulsion is composed of 10% soybean oil and 1.2% egg yolk phospholipids.

6. The pharmaceutical composition of claim 3 wherein the lipid or fat emulsion is composed of 10% soybean oil and 1.2% egg yolk phospholipids.

* * * * *